United States Patent [19]
Ulevitch et al.

[11] Patent Number: 6,010,856
[45] Date of Patent: Jan. 4, 2000

[54] ASSAY SYSTEMS AND METHODS FOR MEASURING P38 MAP KINASE, AND MODULATORS THEREOF

[75] Inventors: Richard J. Ulevitch, Del Mar; Jiahuai Han, San Diego; Yong Jiang, La Jolla; Zhuang-Jei Li, San Diego, all of Calif.

[73] Assignee: The Scripps Research Institute, La Jolla, Calif.

[21] Appl. No.: 08/922,955

[22] Filed: Sep. 3, 1997

[51] Int. Cl.[7] .............................. C12Q 1/68; C12N 15/63; C12N 1/21; C12N 5/10

[52] U.S. Cl. ...................... 435/6; 435/320.1; 435/252.3; 435/325

[58] Field of Search ..................... 435/6, 320.1, 252.3, 435/325

[56] References Cited

PUBLICATIONS

J. Han et al., "Activation of the Transcription Factor MEF2C by the MAP Kinase p38 in Inflammation", Nature 386:296–299, Mar. 1997.
Y. Jiang et al., "Characterization of the Structure and Function of a New Mitogen–Activated Protein Kinase (p38β)", J. Biol. Chem. 271: 17920–6, Jul. 1996.

*Primary Examiner*—Rebecca E. Prouty
*Attorney, Agent, or Firm*—Thomas Fitting; Emily Holmes

[57] ABSTRACT

Assay systems utilizing a reporter construct based on p38 phosphorylation of myocyte enhancer factor 2 (MEF2) transcription factor are provided. The reporter construct and methods of use are provided, as well as methods of treatment of inflammatory and muscular disorders associated with MEF2-regulated gene expression.

14 Claims, 8 Drawing Sheets p38 Activates a Reporter Gene Construct Dependent on MEF-GAL4

The Myocyte Enhancer Factor-2 (MEF2) Family

- Belongs to MADS superfamily

- Binds to A/T rich sequence: CTA[A/T]4TAG/A

- Four members: MEF2A-D

- Homologues in amphibians (SL1/SL2) and drosphilia (D-mef2)

- Contain a MADS box
  (56 aa motif responsible for DNA binding/protein dimerization)
  and a MEF2 domain
  (29aa sequence that may dictate DNA target specificity)

- Interacts as homo-or heterodimers

- MEF2A-D have distinct sequences outside of MADS/MEF2 domains

- Know to regulate expression of muscle-specific genes:
  myosin heavy chain, desmin, M-creatinine kinase . . .

FIG. 8

SEQUENCE LISTING

```
<160> NUMBER OF SEQ ID NOS: 2

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence:  Synthetic
      oligonucleotide probe
<220> FEATURE:
<221> NAME/KEY: misc_feature
<222> LOCATION: (1)..(25)

<400> SEQUENCE: 1
gatcgctcta aaataaccc tgtcg                                          25

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence:  synthetic
      oligonucleotide probe
<220> FEATURE:
<221> NAME/KEY: misc_feature
<222> LOCATION: (1)..(25)

<400> SEQUENCE: 2
gatcgctcta aacataaccc tgtcg                                         25
```

ASSAY SYSTEMS AND METHODS FOR MEASURING P38 MAP KINASE, AND MODULATORS THEREOF

FIELD OF THE INVENTION

The invention relates generally to assay systems and methods for measuring p38 MAP kinase activity and modulators of p38 MAP kinase activity, and more particularly to methods for measuring the specific interactions, and modulators thereof, between p38 MAP kinase and transcription factors such as MEF2C.

BACKGROUND

Activation of members of the mitogen-activated protein kinase (MAPK) family represents one of the major mechanisms used by eukaryotic cells to transduce extracellular signals into cellular response (J. Blenis, *Proc. Natl. Acad. Sci. USA* 90, 5889 (1993); K. J. Blumer et al., *TIBS,* 19, 236 (1994); E. Cano et al., *TIBS* 20, 117 (1995); R. Seger et al., *FASEB J.* 9, 726 (1995); R. J. Davis, *TIBS* 19, 470 (1994)). One member of this kinase family, p38, has been implicated in signaling pathways used by biologically important stimuli including products of microbial pathogens, cytokines, UV light and increased extracellular osmolarity. Most recently p38 activation was found to be correlated with apoptosis in neuronal cells following withdrawal of nerve growth. p38 is activated by a subset of the known dual specificity MAPK kinases (MEKs or MKKs); low molecular weight GTP-binding proteins RAC1 and Cdc42 have also been shown to play a role in regulating p38 activation by some stimuli. A complete understanding of how p38 activation regulates cellular responses requires identification of specific substrates for this enzyme.

SUMMARY

The present invention is based on the elucidation of the mechanisms whereby p38 activation regulates cellular responses and identification of substrates for the kinase. As shown by the present invention, a target for interaction with p38 is the transcription factor MEF2C. Transcription factors are required for gene expression, and are known to regulate classes of transcriptional activity. The MEF2C is a member of the myocyte enhancer factor (MEF) transcription factor family, designated MEF2.

p38 is a MAP kinase (MAPK) implicated in many cell processes including cytokine induction and apoptosis. By using a two-hybrid screen, the inventors have identified MEF2C, a member of MEF2 transcription factor family, as a substrate selectively phosphorylated by p38. p38 modifies the activity of MEF2C by changing its interaction with oligonucleotides containing a MEF2C consensus site and by increasing MEF2C-mediated transcriptional activity. These findings point out unsuspected roles for MEF2C-dependent gene regulation.

In a first embodiment, the invention provides a p38 MAP kinase reporter gene construct which includes: a) a nucleotide sequence defining a reporter gene capable of expressing a detectable gene product upon expression; b) a nucleotide sequence operatively linked to the reporter gene defining a TATA box capable of binding a first transcription factor which interacts with and is activated by a phosphorylated second transcription factor; and c) a nucleotide sequence operatively linked to the TATA box that defines a DNA binding site for a DNA binding protein that contains a second transcription factor domain that is a phosphorylation substrate for p38 MAP kinase. Upon phosphorylation by p38 MAP kinase, the DNA binding protein binds to the DNA binding site and interacts with the first transcription factor bound to the TATA box, thereby activating expression of the reporter gene.

In another embodiment the invention provides a method for measuring the effect of a component on the p38 MAP kinase pathway in a reporter system. The method includes contacting a sample containing the component with a p38 MAP kinase reporter gene construct as described above, under conditions compatible with phosphorylation and gene expression in an expression admixture; maintaining the expression admixture under conditions sufficient for the phosphorylation and reporter gene expression; and measuring the amount of expressed reporter gene, and thereby measuring the effect of the component on the p38 MAP kinase pathway.

In yet another embodiment, the invention includes a method of treating a subject having a p38/MEF2 associated disorder comprising administering to the subject a therapeutically effective amount of a p38/MEF2 modulating reagent that affects phosphorylation of MEF2. Such disorders include inflammatory, neural, apoptotic and muscle related diseases.

DETAILED DESCRIPTION OF THE INVENTION

The interaction between p38 and MEF2C identified by the present invention has allowed the development of a variety of systems and assays for measuring components active in the p38 signaling pathway and for measuring components active in the interaction between p38 and MEF2C.

Figure 5:
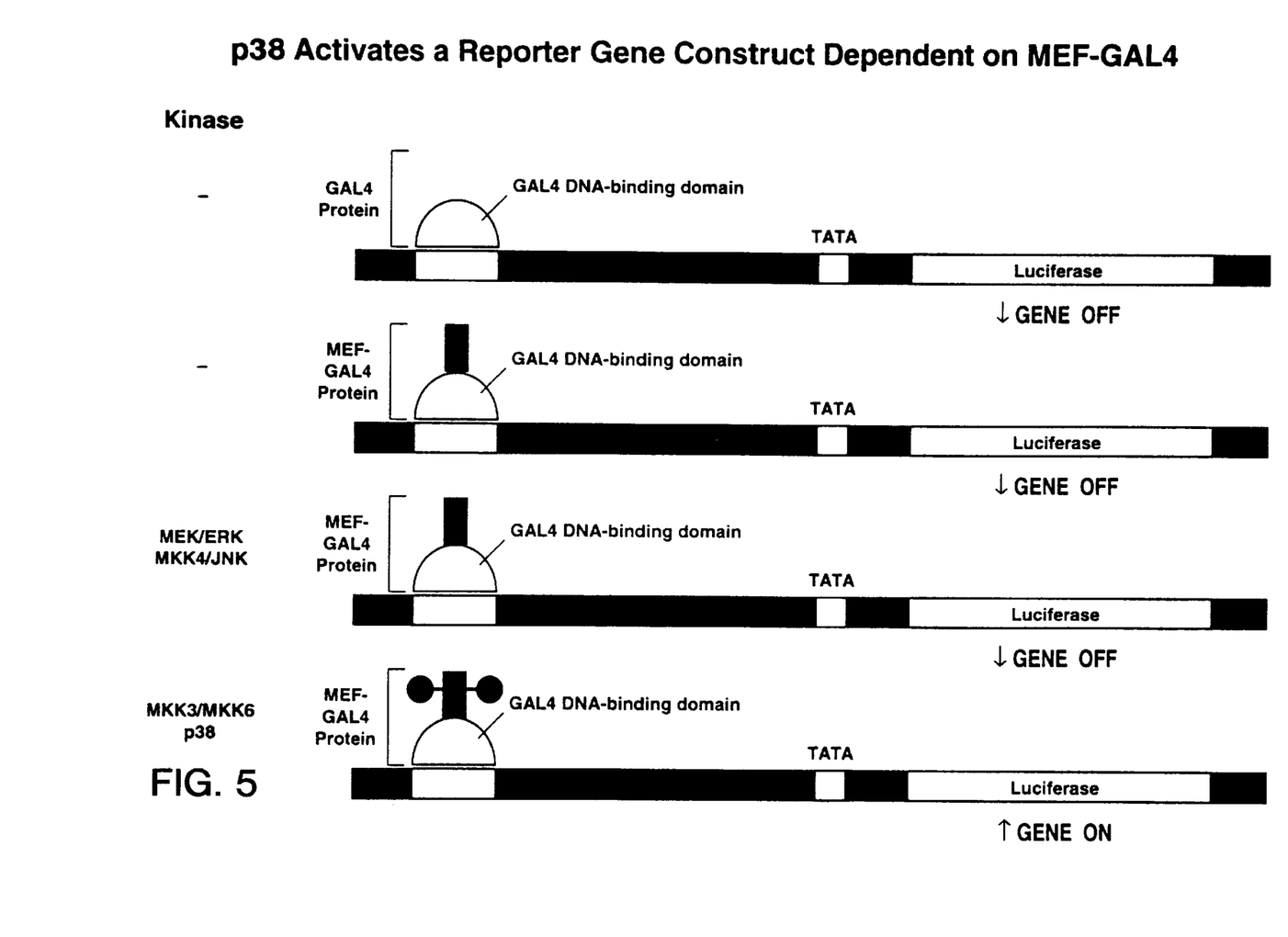
FIG. 5 is an illustration of reporter gene constructs of the invention.

The details of the interaction between p38 and MEF2C are described in the accompanying Examples and Figures. Specifically, FIG. 5 illustrates results using a p38 MAP kinase pathway reporter gene construct according to the present invention for assaying the activity of p38 MAP kinase using a transcription factor that is a substrate for p38 MAP kinase (MEL-GAL4 fusion protein) which, upon phosphorylation can interact with the construct to activate expression of the luciferase gene product. Luciferase is then assayed by standard methods. In the top row, a control construct is illustrated in which there is no transcription factor/p38 MAP kinase substrate in the fusion protein (designated "GAL4 protein"). There is no gene expression, even in the presence of p38 MAP kinase, indicating that the construct is specific and cannot function without a substrate.

In the second row of FIG. 5, there is no gene expression observed because the assay was run in a cell that did not contain any MAP kinase, indicating that the elements of the assay system are not leaky to expression in the absence of p38 MAP kinase.

In the third row of FIG. 5, the host cell in which the assay is run ("MEK" or "ERK") does not produce p38 MAP kinase, but instead produces the MAP kinase designated "MKK/JNK" having a different substrate specificity that is not reactive with the MEF2C substrate in the MEF-GAL4 protein. The results show that although all the elements of the reporter construct are present, the kinase must be p38 MAP kinase based on the specificity of the substrate in the second transcription factor (i.e., the MEF-GAL4 fusion protein). The fourth row illustrates gene expression using a reporter gene construct as claimed in the presence of a cell line that produces p38 MAP kinase (MKK3/MKK6).

Figure 6:
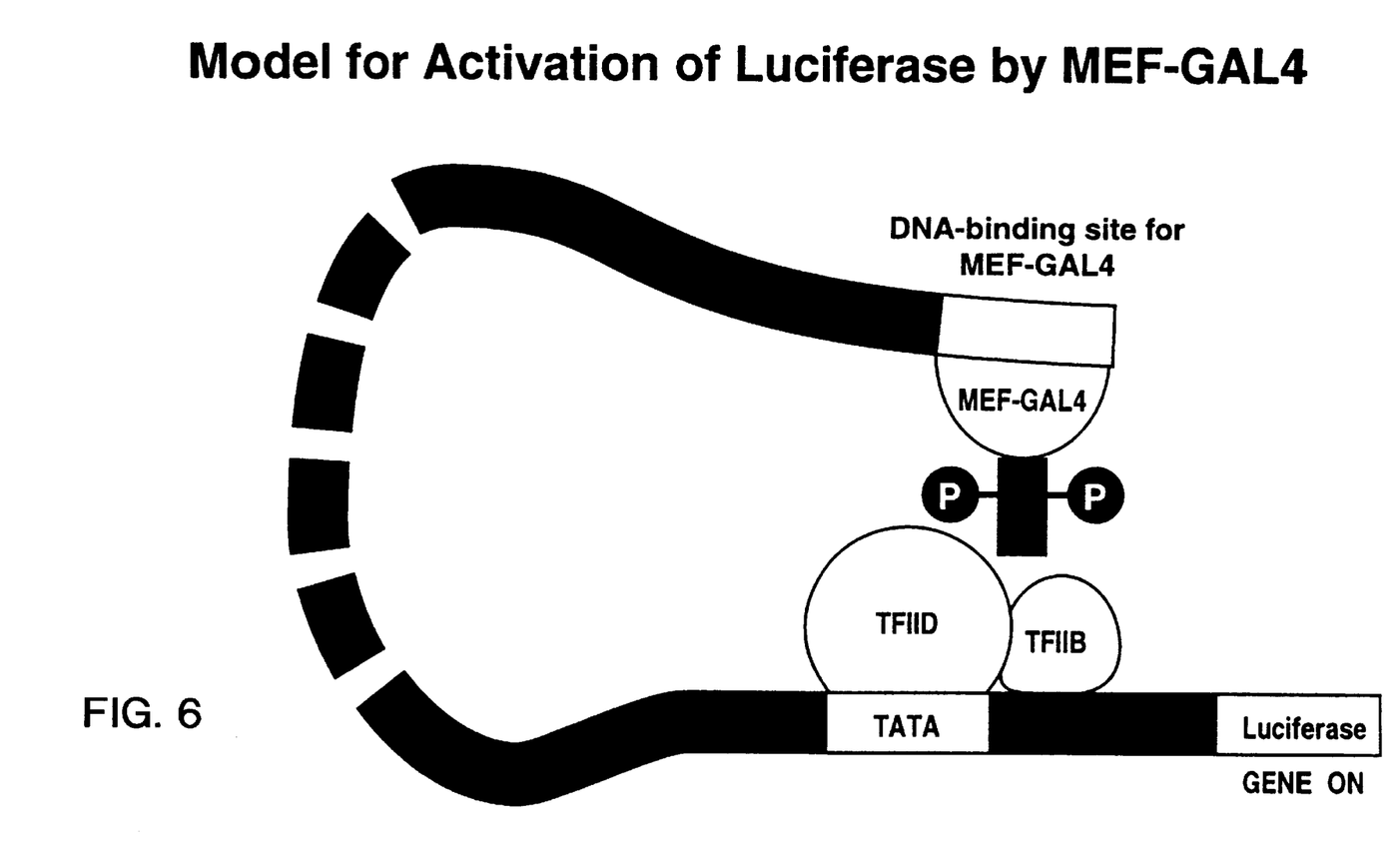
FIG. 6 is a schematic illustration for activation of a reporter gene by MEF-Gal4.

FIG. 6 is a schematic of the reporter gene construct of the present invention illustrating how the phosphorylated DNA binding protein (MEF-GAL4) activates the first transcriptional promoter complexed on the TATA box to express the luciferase gene.

Figure 7:
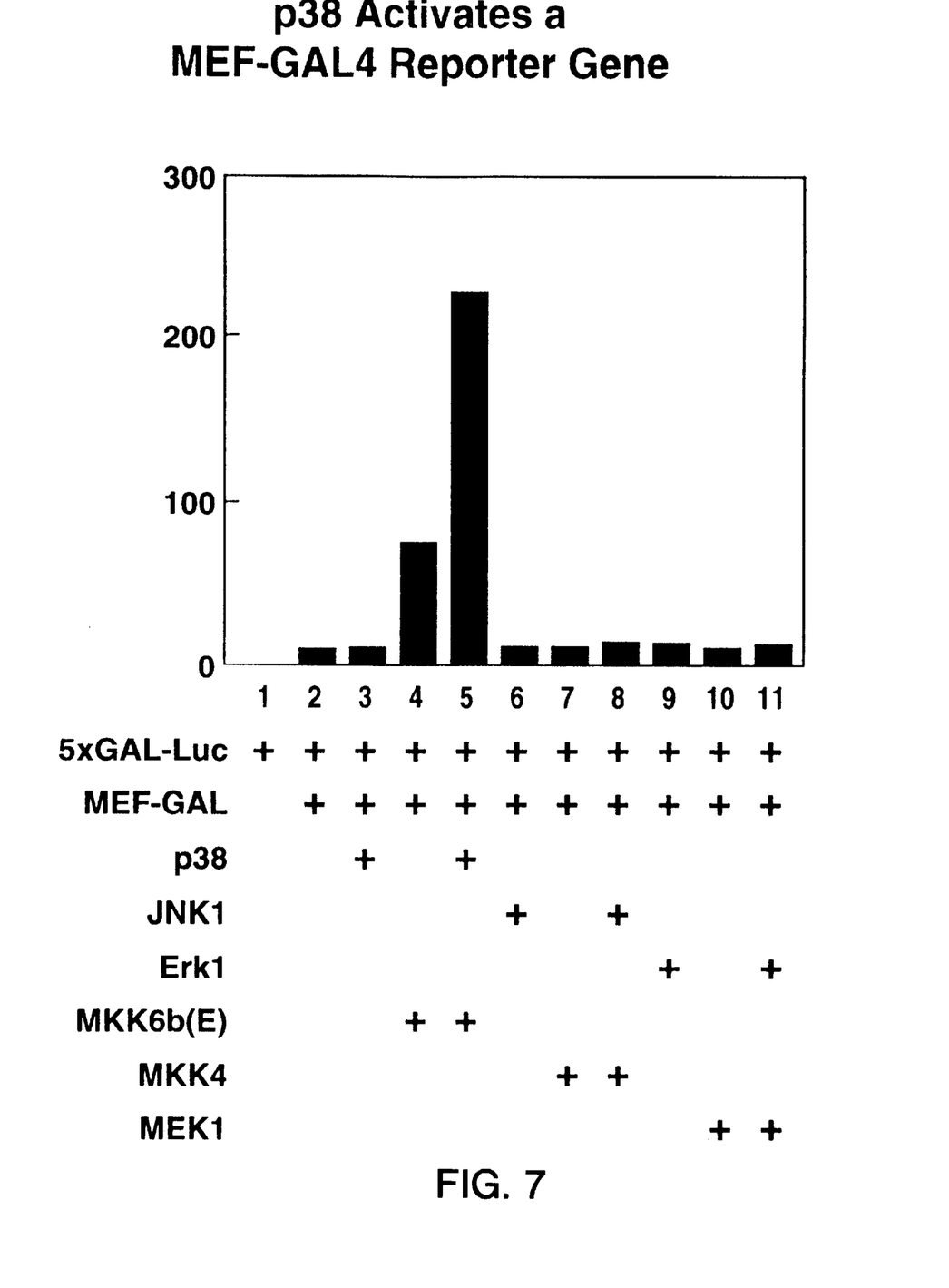
FIG. 7 shows p38 activation of the reporter gene versus other protein kinases.

FIG. 7 is a table illustrating the activation of the MEF-GAL4 reporter gene construct by p38 MAP kinase in HeLa cells. The bar graph illustrated from 0 to 300 arbitrary units of expressed luciferase gene product, including data from 11 different experimental conditions in which the listed components are included in the expression admixture as indicate by "+". "5xGAL-Luc" is the nucleic acid vector having the luciferase reporter gene construct shown in FIG. 6. "MEF-GAL" indicates the addition of a plasmid to the HeLa cells which expresses the MEF-GAL4 protein that functions as the second transcription factor and p38 MAP kinase substrate. "p38" indicates the addition of a plasmid to the HeLa cells which expresses p38 MAP kinase protein able to phosphorylate the substrate once p38 MAP kinase itself is activated (by phosphorylation). "JNK1" indicates the addition of a plasmid to the HeLa cells that expresses the kinase JNK1 which is typically activated by the kinase kinase MKK4. "Erk1" indicates the addition of a plasmid to the HeLa cells that expresses the kinase Erk1 which is typically activated by the kinase kinase MEK1. "MKK6b(E)" indicates the addition of a plasmid to the HeLa cells that expresses the kinase kinase MKK6b(E) which typically activates p38 MAP kinase. "MKK4" indicates the addition of a plasmid to the HeLa cells that expresses the kinase kinase MKK4 which typically activates JNK1. "MKK1" indicates the addition of a plasmid to the HeLa cells that expresses the kinase kinase MKK1 which typically activates Erk1.

Collectively, the data in FIG. 7 indicate that only p38 MAP kinase can activate the subject reporter gene in the presence of the p38 MAP kinase substrate (DNA binding protein) protein MEF-GAL4. The other kinases JNK1 and Erk1 are not active in the reporter system because the phosphorylation substrate domain of MEF2C is not a substrate for these other kinases, indicating the specificity of the system.

Figure 8:
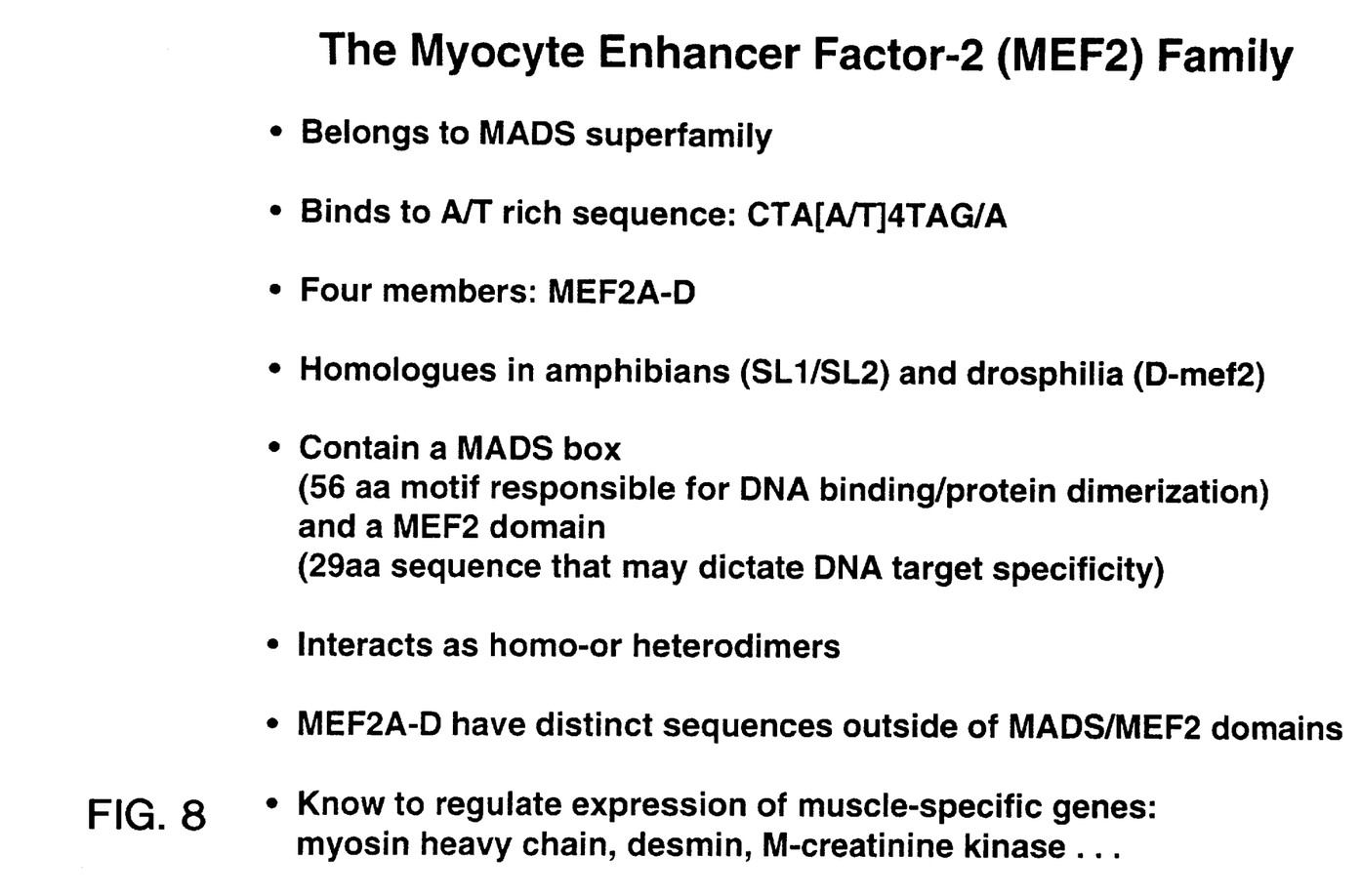
FIG. 8 is a table that provides a description of the myocyte enhancer factor-2 (MEF2) family.

FIG. 8 displays a table of information about the MEF2 family of transcription factors that includes MEF2C.

The invention contemplates a variety of formats for analysis of the activity of components that function in the p38 MAP kinase pathway. In one embodiment, the invention contemplates a method to assay for any component which affects the pathway using a reporter gene construct as exemplified in the Examples and in FIG. 5 and FIG. 6. In this format, a reporter gene encodes any detectable gene product whose expression is related to the ability of p38 MAP kinase to effect expression of the gene construct. The transcriptional control elements are p38 MAP kinase-specific, and therefore, any effect measured by expression of the reporter gene indicates an effect on the p38 MAP kinase pathway.

The transcriptional control elements include a TATA box, which is a sequence on nucleotides capable of binding the transcription factors TFIID and TFIIB (i.e., a first transcription factor) to form a transcription complex which upon activation by p38 MAP kinase-phosphorylated transcription factor (i.e., a second transcription factor), results in expression of the reporter gene. The TATA box is operatively linked to the reporter gene in a manner to allow the transcription complex to control expression of the reporter gene.

The reporter gene construct also includes a DNA-binding site for a DNA binding protein that includes the function of the second transcription factor which also regulatable as a p38 MAP kinase substrate for phosphorylation. The DNA binding protein can be any of a variety of p38 MAP kinase substrates so long as it includes the ability to activate the transcription complex upon phosphorylation by p38 MAP kinase. Any DNA binding site nucleotide sequence can be used that is able to bind the DNA binding protein. The DNA binding protein can be a fusion protein, combining a DNA binding site domain with a transcription factor domain that is a substrate for p38 MAP kinase. A preferred DNA binding protein includes the MEF2C transcription factor domain. Particularly preferred is the fusion protein shown in FIG. 5.

A reporter gene can encode any of a variety of detectable gene products, and therefore, the invention need not be limited in this regard. Preferred detectable gene products are enzymes, biologically active proteins, and the like. Particularly preferred are beta-galactosidase which produces a visual dye, luciferase, or the green fluorescent protein of the bioluminescent jellyfish *Aequorea victoria,* which produce fluorescent green light. Chalfie et al., *Science,* 263:802–804 (1994).

The invention can be practiced in vitro or in a cellular environment. In vitro, the various expression admixture components to support a p38 MAP kinase reaction and to support gene expression, including the relevant transcription factors, must be provided, as is well known. Alternatively, the expression admixture can be provided in a cell, such as yeast, bacterial or mammalian cells adapted for culture.

In assay formats to measure the amount of p38 MAP kinase, the sample added to the expression admixture is believed to contain p38 MAP kinase, and expression is related to the amount of added p38, all other materials being present in the expression admixture for phosphorylation of the second transcription factor and expression of the reporter gene.

In other assay formats to measure a component that modulates p38 MAP kinase activity, such as an inhibitor of p38 MAP kinase, control assay reactions are run in the presence and absence of p38 MAP kinase and in the presence and absence of the modulator substance to be measured. This format is particularly well suited as a screening procedure for inhibitors or modulators of p38 MAP kinase.

In another assay format where the second transcription factor is MEF2C, the assay is well suited for measuring specific interactions between p38 MAP kinase and the MEF2C transcription factor or for screening for components which modulate MEF2C directly.

Also contemplated are nucleic acid constructs which comprise the reporter gene constructs described herein for assaying component effects on the p38 MAP kinase pathway. The p38 MAP kinase reporter gene construct can have any of a variety elements as described herein. Particularly preferred are the constructs illustrated in FIG. 5 and FIG. 6.

In addition, the invention contemplates a cell or cell line containing a reporter gene construct of the present invention. The cell line can be a bacterial cell, a yeast cell, a mammalian cell adapted for culture, including but not limited to a HeLa cell, a Jurkat cell, a lymphoid cell, and the like.

Also contemplated are kits for practicing the invention, which can include the reporter gene construct of the present invention. Instructions for use are also typically included. The kit may further contain components for constituting the expression admixture including, but not limited to, ATP, p38 MAP kinase, reporter gene product (as a control), phosphorylation/expression buffers, and the like. Thus, the materials of the invention are ideally suited for the preparation of a kit for the detection of the level of MEF2 phosphorylation or MEF2 regulated gene transcription.

In one embodiment, activation of the p38 signal transduction pathway is determined by measuring phosphorylation of MEF2C. p38 activity is measured by the rate of substrate (i.e., MEF2C) phosphorylation as determined by quantitation of the rate of labelled phosphorus (e.g., [$^{32}$]P or [$^{33}$]P) incorporation for example. This can also be measured using phosphorylation-specific reagents, such as antibodies. The specificity of p38 substrate phosphorylation can be tested by measuring MEF2C phosphorylation or MEF2C-regulated gene expression, or by employing mutated MEF2C molecules that lack the sites for p38 phosphorylations or mutated p38 (see Examples). Altered phosphorylation of the substrate relative to control values indicates alteration of the p38 signal transduction pathway, and increased risk in a subject of a disorder associated with p38/MEF2C interaction or MEF2-regulated gene expression.

In another embodiment, the invention contemplates a system for studying the binding interaction between p38 MAP kinase and MEF2C. Such a binding interaction is illustrated in the Examples where agarose-immobilized p38 MAP kinase is used to study the binding interaction with MEF2C. In such a format, the system can be used to screen for modified p38 MAP kinase proteins or modified MEF2C proteins with retained or altered abilities to interact. In this format, one can also screen for compounds which perturb the binding interaction between p38 MAP kinase and MEF2C.

Thus, in one embodiment, the present invention relates to binding agents that interfere with binding between p38 and MEF2C. Such binding agents may interfere by competitive inhibition, by non-competitive inhibition or by uncompetitive inhibition.

Incubating includes conditions which allow contact between the test composition and p38 and MEF2. Contacting includes in solution and in solid phase. The test composition may optionally be a combinatorial library for screening a plurality of compositions. Compositions identified in the method of the invention can be further evaluated, detected, cloned, sequenced, and the like, either in solution or after binding to a solid support, by any method usually applied to the detection of a specific DNA sequence such as PCR, oligomer restriction (Saiki, et al., *Bio/Technology*, 3:1008–1012, 1985), allele-specific oligonucleotide (ASO) probe analysis (Conner, et al., *Proc. Natl. Acad. Sci. USA*, 80:278, 1983), oligonucleotide ligation assays (OLAs) (Landegren, et al., *Science*, 241:1077, 1988), and the like. Molecular techniques for DNA analysis have been reviewed (Landegren, et al., *Science*, 242:229–237, 1988).

To determine if a composition can functionally affect the p38/MEF2C complex, a reporter gene construct as described above is preferably utilized. Transcription of the reporter or of the exogenous gene is monitored by monitoring changes in the protein levels of the protein encoded for by the exogenous gene, for example. When a composition(s) is found that does not affect transcription of the reporter gene, it is concluded that this composition(s) does not block or bind p38/MEF2C.

Expression of the reporter gene can be monitored by a functional assay or assay for a protein product, for example. The exogenous gene is therefore a gene which will provide an assayable/measurable expression product in order to allow detection of expression of the exogenous gene. Such exogenous genes include, but are not limited to, reporter genes such as chloramphenicol acetyltransferase gene, an alkaline phosphatase gene, beta-galactosidase, a luciferase gene, a green fluorescent protein gene, guanine xanthine phosphoribosyltransferase, alkaline phosphatase, and antibiotic resistance genes (e.g., neomycin phosphotransferase).

Lack of expression of the reporter gene in the presence of the composition, as opposed to in the absence of the reporter, is indicative of composition binding, thus, the binding or blocking composition can be identified and isolated. The compositions of the present invention can be extracted and purified from the culture media or a cell by using known protein purification techniques commonly employed, such as extraction, precipitation, ion exchange chromatography, affinity chromatography, gel filtration and the like. Compositions can be isolated by affinity chromatography using the modified receptor protein extracellular domain bound to a column matrix or by heparin chromatography.

Also included in the screening method of the invention is combinatorial chemistry methods for identifying chemical compounds that bind to or block p38/MEF2C interaction.

In yet another embodiment, the invention provides a method for treating a subject having a disorder associated with MEF2C regulated transcription. The method includes modulating p38/MEF2C interaction thereby modulating MEF2C-dependent gene expression. Modulation of p38/MEF2C includes inhibitory or stimulatory effects. Disorders in which MEF2C causes increased or decreased transcription from an enhancer or a promoter containing an MEF2C or MEF2C-like concensus motif are subject to treatment by the method of the invention. Such disorders include inflammatory disorders, including infection, and muscular disorders, for example. A blocking or binding agent which inhibits p38/MEF2C binding, and therefore, MEF2C phosphorylation, may have applications in treating disease processes involving muscle, such as in musculodegenerative diseases or in tissue repair due to trauma. Since myoblast cells may be used as a vehicle for delivering genes to muscle for gene therapy, the properties of the p38/MEF2C interaction could be exploited for gene expression both prior to transplantation or for enhancing gene expression after transplantation. Modulation of expression of p38/MEF2C-dependent gene expression may be in any cell in which p38 and MEF2 are expressed, such as muscle cells, brain cells (e.g., neural cells), spleen cells, monocytes and macrophages.

By using an RNA protection assay, the inventors have detected abundant MEF2C transcripts in primary monocytes and macrophage cell lines. Interference with normal binding between p38 and MEF2 may result in a useful pharmacological effect related to inflammation. Many cytokine genes (e.g., IFN$\alpha$ and IL-1$\beta$) contain MEF2 or MEF2-like consensus motifs. Therefore, MEF2C may participate in the regulation of cytokine gene expression in monocytes or macrophages. Thus, p38/MEF2C interaction, or modulation of the interaction may regulate monocyte accumulation and activation in inflamed tissue sites. Monocytes are long-lived cells capable of further differentiation as they move from the blood to establish residence in the tissues as macrophages. The functional properties of tissue macrophages differ in different organs, and in the same organ depending on the presence of priming agents, i.e., agents that can change the behavior of monocytes and make them more sensitive to chemokines or chemoattractants. p38/MEF2C-binding or blocking agents can interfere with the normal functioning of this system to reduce inflammation and are contemplated by the present invention. Antibodies, peptides, peptidomimetics, polypeptides, chemical compounds and biologic agents that interfere with this interaction are also useful in this context.

A "p38/MEF2C associated disorder" is a pathological condition resulting, at least in part, from excessive activation of a p38/MEF2C signal transduction pathway. The p38/MEF2C signal transduction pathways are activated by several factors, including inflammation and stress. p38/MEF2C-mediated disorders include, for example, ischemic heart disease, burns due to heat or radiation (UV, X-ray, $\gamma$, $\beta$, etc.), kidney failure, liver damage due to oxidative stress or alcohol, infection, respiratory distress syndrome, septic shock, rheumatoid arthritis, autoimmune disorders, and other types of inflammatory diseases.

A "therapeutic reagent" may be any compound or molecule that achieves the desired effect on a p38/MEF2C mediated disorder when administered to a subject in need thereof.

p38/MEF2C mediated disorders further include proliferative disorders, particularly disorders that are stress-related. Examples of stress-related p38/MEF2C-mediated proliferative disorders are psoriasis, acquired immune deficiency syndrome, malignancies of various tissues of the body, including malignancies of the skin, bone marrow, lung, liver, breast, gastrointestinal system, and genito-urinary tract. Preferably, therapeutic reagents inhibit the activity or expression of p38 or MEF2C inhibit cell growth or cause apoptosis.

A therapeutic reagent that "inhibits p38/MEF2C activity" interferes with a p38/MEF2-mediated signal transduction pathway. For example, a therapeutic reagent can alter the protein kinase activity of p38, decrease the level of p38 or MEF2 transcription or translation, or suppress p38 phosphorylation of MEF2C, thus disrupting the p38/MEF2C-mediated signal transduction pathway. Examples of such reagents include antibodies that bind specifically to p38 or MEF2 polypeptides, and fragments of p38 or MEF2C polypeptides that competitively inhibit the interaction between p38 and MEF2C.

A therapeutic reagent that "enhances p38/MEF2C activity" supplements a p38/MEF2C-mediated signal transduction pathway. Examples of such reagents include the p38 or MEF2C polypeptides themselves, which can be administered in instances where the p38/MEF2C-mediated disorder is caused by under expression of the p38 or MEF2C polypeptide, or expression of a mutant p38 or MEF2C polypeptide. In addition, portions of DNA encoding a p38 or MEF2C polypeptide can be introduced into cells that under-express a p38 or MEF2C polypeptide.

A "therapeutically effective amount" is an amount of a reagent sufficient to decrease or prevent the symptoms associated with the p38/MEF2C-mediated disorder.

Therapeutic reagents for treatment of p38/MEF2C-mediated disorders identified by the methods of the invention are administered to a subject in a number of ways known to the art, including parenterally by injection, infusion, sustained-release injection or implant, intravenously, intraperitoneally, intramuscularly, subcutaneously, or transdermally. Epidermal disorders and disorders of the epithelial tissues are treated by topical application of the reagent. The reagent is mixed with other compounds to improve stability and efficiency of delivery (e.g., liposomes, preservatives, or dimethyl sulfoxide (DMSO)). Polynucleotide sequences, including antisense sequences, can be therapeutically administered by techniques known to the art resulting in introduction into the cells of a subject suffering from the p38/MEF2—mediated disorder. These methods include the use of viral vectors (e.g., retrovirus, adenovirus, vaccinia virus, or herpes virus), colloid dispersions, and liposomes.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting.

Other features and advantages of the invention will be apparent from the detailed description, and from the claims.

EXAMPLE 1

Figure 1A:
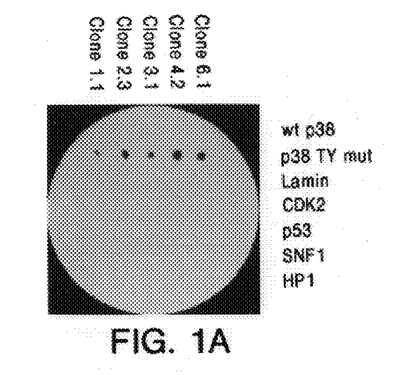
FIG. 1A is an X-gal colony filter assay showing β-gal reporter gene expression. The β-gal activity of lifted yeast clones which mated from indicated transformants are shown.

To identify proteins that interact with p38, a yeast two-hybrid system was used. Two constructs of p38, produced by fusing the cDNA of the p38 coding region (wtp38) or a p38 mutant with the TGY dual phosphorylation site mutated to AGF (TY mutant) to the C-terminus of the Gal4 DNA-binding domain in the pAS1 vector (T. Durfee et al., *Genes and Develop.* 7, 555 (1993), were used as targets in the two-hybrid screen. A human fetal brain cDNA library fused with the Gal4 activation domain placed in the pGAD10 vector (ClonTech) was screened using each of the two target constructs. The interaction was detected by growth on medium lacking histidine and by expression of $\beta$-galactosidase ($\beta$-gal) activity. After screening 1×10$^7$ transformants with wtp38 or the TY mutant five positive clones were identified that interacted with the TY mutant; no clones were obtained with wtp38. This result may be due to a transient interaction between enzymatically active p38 and its substrate(s); the enzyme-dead mutant may form a more stable complex with its binding partners facilitating detection in the two-hybrid system. To address the specificity of this selection, a mating experiment was performed. The cDNAs from five isolated clones were transfected into yeast strain Y190 and the resultant cells were mated with strain Y187 transfected with cDNAs encoding wtp38, the p38 TY mutant, lamin, CDK2, p53, SNF1, and HP1 fused with the Gal4 DNA binding domain in the pAS1 vector (T. Durfee et al., *Genes and Develop.* 7, 555 (1993)). A colony filter assay was used to test β-gal activity in mated yeast (FIG. 1A). The mated yeasts were selected by growing in SD medium minus Leu and Trp (T. Durfee et al., *Genes and Develop.* 7, 555 (1993). The interaction of the two proteins was judged by β-gal reporter gene expression. A X-gal colony filter assay was used to determine β-gal activity ((T. Durfee et al., *Genes and Develop.* 7, 555 (1993)). The β-gal activity of lifted yeast clones which mated from indicated transformants are shown.

Figure 1B:
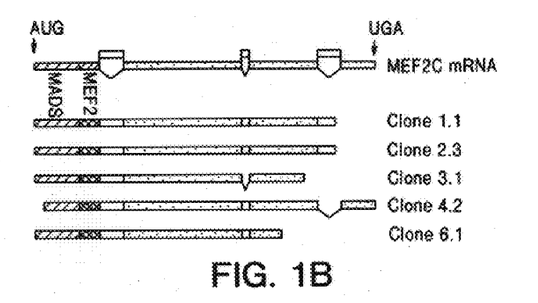
FIG. 1B is a schematic diagram of the insert in the five isolated MEF2C clones. The boundaries of MADS and MEF2 boxes are indicated. The alternatively spliced regions are shown by the open boxes.

As judged by β-gal activity no interactions were observed except when the TY mutant was present with any of the five isolated clones. The cDNA from each of the five clones was sequenced and all encoded different regions of the same protein; namely, myocyte-enhancer factor 2C (MEF2C) (J. F. Martin et al., *Proc. Natl. Acad. Sci. USA* 90, 5282 (1993); J. C. McDermott et al., *Mol. Cell. Biol.* 13, 2564 (1994); D. Leifer et al., *Proc. Natl. Acad. Sci. USA* 90, 11546 (1993)). A schematic diagram of the five clones is shown in FIG. 1B. The boundaries of MADS and MEF2 boxes are indicated. The alternatively spliced regions are shown by the open boxes.

MEF2C is a transcription factor belong to the MEF2 subfamily of the MADS (MADS is named for the yeast mating-type specific transcription factor MCM1, two plant homeotic genes agamous and deficiens, and human serum response factor SRF.) gene family. MEF2C has three alternatively spliced exons. The first was found in all our clones; alternatively spliced exons two or three were not found in some of the clones (FIG. 1B). Thus the second and third alternatively spliced exons are not required for interaction between MEF2C and p38. There are four members of MEF2 family genes which have been cloned (R. E. Breitbart et al., *Development* 118, 1095 (1993); J. F. Martin et al., *Mole. Cell. Biol.* 14, 1647 (1994)). These four proteins share greater than 85% identity within the MADS and MEF2 domains. The regions outside of these two domains differ but still share a high level of homology. The interaction with p38 seems selective for MEF2C because no other members of this family have been isolated by the two-hybrid screening; the cDNAs encoding these other family members are present in the brain library used in this study.

EXAMPLE 2

To examine if there is a physical interaction of wtp38 with MEF2C an approach combining a solid-phase binding and phosphorylation assay was used. In this experiment wtp38 was used to insure that the interaction detected in the two-hybrid system was not limited to the p38 TY mutant. Recombinant GST-wtp38 bound to glutathione-agarose was prepared and then incubated this complex with increasing amounts of recombinant MEF2C in the presence or absence of ATP. Immunoblotting revealed saturable binding of MEF2C to GST-wtp38-agarose but not GST-agarose (FIG. 1C, middle panel).

The interaction of p38 with MEF2C demonstrated by a solid phase binding assay. 1 μg recombinant GST fusion protein of p38 (GST-wtp38) was bound to glutathione-agarose. The beads were incubated with different amount of His-tagged recombinant MEF2C (The entire coding region of MEF2C cDNA without last alternatively spliced exon was subcloned into pET14b using XhoI and BamHI sites. The recombinant protein was prepared as described (D. J. Robbins et al., *J. Biol. Chem.* 268, 5097 (1993)) in buffer A containing 2% BSA (Buffer A: 10 mM Tris-HCl, pH7.9, 250 mM NaCl, 25 mM imidazole, and 0.05% Triton-X-100) with or without cold ATP (20 μM) for 3 h after blocking the nonspecific binding with 2% BSA in buffer A for 3 h. After washing the beads 6 times with buffer A, one-half of the sample was analyzed by immunoblotting; His-MEF2C was detected using Ni-NTA conjugated with alkaline phosphatase (Qiagen) (shown in middle panel), and GST-p38 was detected with rabbit anti-p38 antibody together with peroxidase coupled to sheep anti-rabbit IgG (Cappel) (shown in upper panel). The remaining sample was used in a solid-phase kinase assay by incubating with γ-$^{32}$P-ATP as described (B. Derijard et al., *Cell* 76, 1025 (1994)). The phosphorylation of MEF2C bound to GST-p38-beads was shown in the lower panel.

Figure 1C:
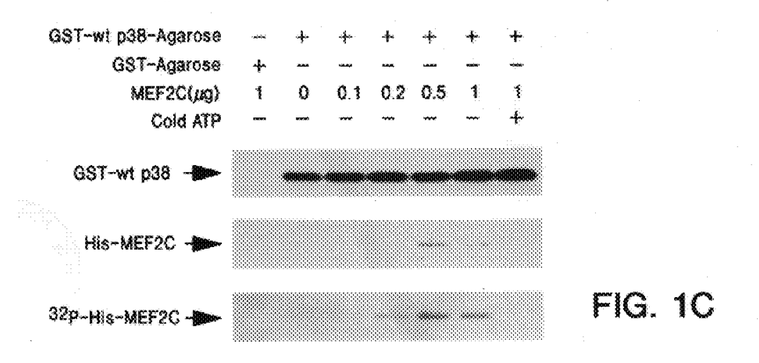
FIG. 1C is an immunoblot and a solid-phase kinase assay showing phosphorylation of MEF2C bound to GST-p38-beads.

The binding of MEF2C to p38 was not detected when ATP was included (FIG. 1C; middle panel, last lane). Phosphorylation of the bound MEF2C can be achieved by incubation of the mixture with γ-$^{32}$P-ATP (FIG. 1C, lower panel). These data support our interpretation of findings from the two-hybrid screen where no interaction between wtp38 and MEF2C was detected.

EXAMPLE 3

Figure 2:
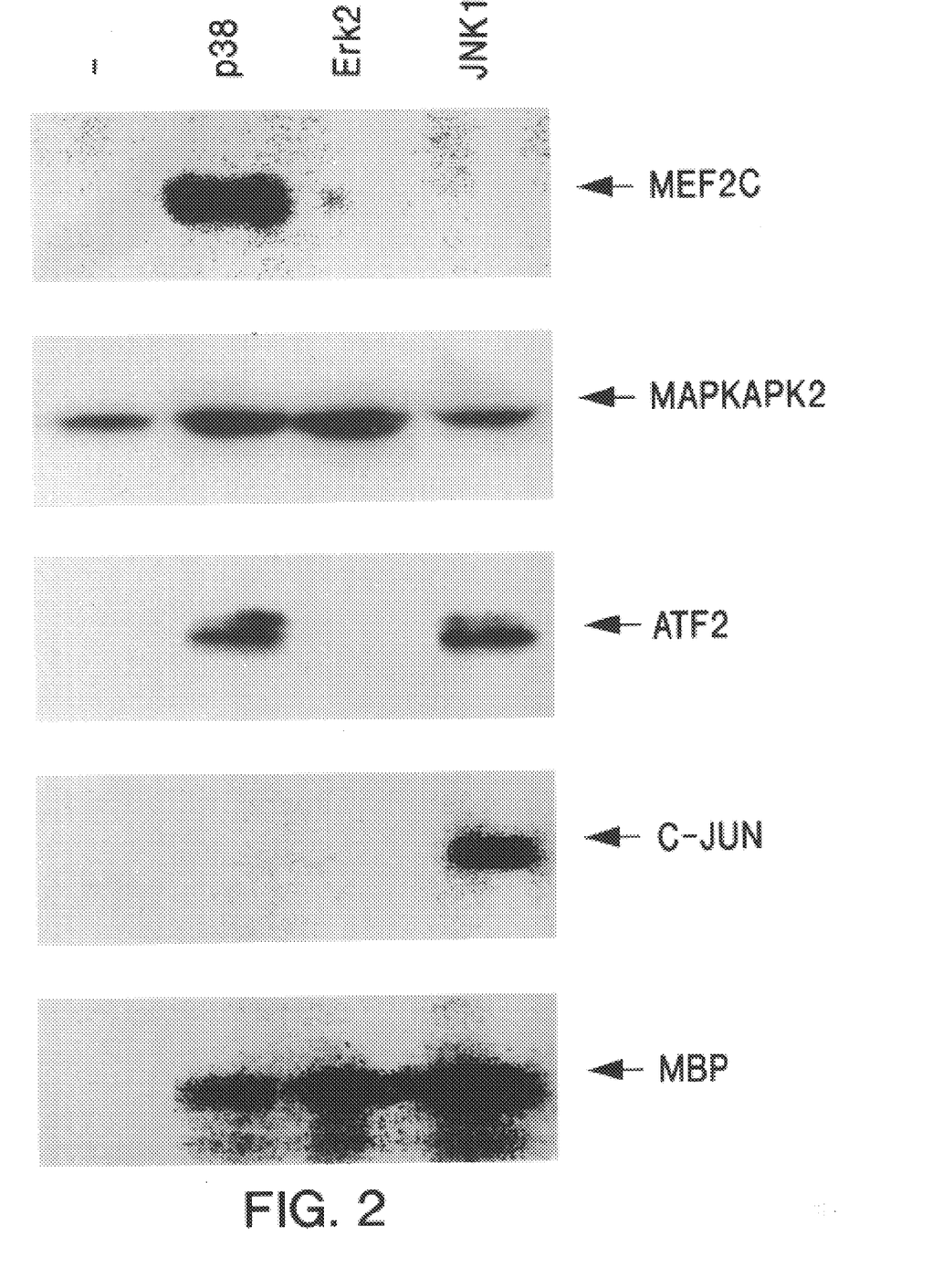
FIG. 2 shows the extent of phosphorylation of various substrates as quantified by phosphorimaging.

Although a number of proteins can be phosphorylated by p38 (J. Raingeaud et al., *J. Biol. Chem.* 270, 7420 (1995); N. W. Freshney et al., *Cell,* 78, 1039 (1994); J. Rouse et al., *Cell* 78, 1027 (1994)), MEF2C should be preferred when compared to other proteins if it is a physiological substrate. An in vitro kinase assay comparing the following recombinant proteins as substrates was used; MAP kinase activated protein kinase 2 (MAPKAPK2), the amino-terminal protein (residues 1–109) of activating transcription factor 2 (ATF2), the amino terminal portion of c-Jun (residues 1–93), myelin basic protein (MBP) and MEF2C. The activity of recombinant p38 on these proteins was also compared with two other MAPK family members; recombinant extracellular regulated protein kinase 2 (ERK2) and c-Jun N-terminal kinase 1 (JNK1). Equal amounts of the substrate proteins were used in the in vitro kinase assay (FIG. 2); importantly these studies revealed MEF2C is the preferred substrate of p38. Other substrate preferences were observed for ERK2 or JNK1 (FIG. 2).

Equal amounts of (0.5 μg) of His-MEF2C, GST-MAPKAPK2 (Y. -L. Zu et al., *Biochem. Biophys. Res. Comm.* 200, 1118 (1994)), GST-ATF2 (residues 1–109) (J. Han et al., *J. Biol. Chem.* (1996), in press), GST-c-Jun (residues 1–93) (B. Derijard et al., *Cell* 76, 1025 (1994)), or MBP (sigma) were used as substrates. Recombinant His-tagged wtp38 (J. Han et al., *Science* 265, 808 (1994)), His-tagged ERK2 (D. J. Robbins et al., *J. Biol. Chem.* 268, 5097 (1993), or flag-tagged JNK1 (B. Derijard et al., *Cell* 76, 1025 (1994)) were used as kinases. The kinase reactions were performed with γ-$^{32}$P-ATP as described (J. Han et al., *J. Biol. Chem.* (1996), in press; B. Derijard et al., *Cell* 76, 1025 (1994)). The incorporation of $^{32}$p into MAPKAPK2 in the absence of added enzymes is due to autophosphorylation. The extent of phosphorylation was quantified by phosphorimaging.

The phosphorylation level of MEF2C was quantitated using the phosphorimager; the activity of p38 toward MEF2C is estimated to be 16-fold higher than ERK2 and 100-fold higher than JNK1 after normalizing the three enzyme activities toward MBP. These data further support the contention that the p38-MEF2C interaction is specific and likely to reflect a physiological interaction.

EXAMPLE 4

Figure 3:
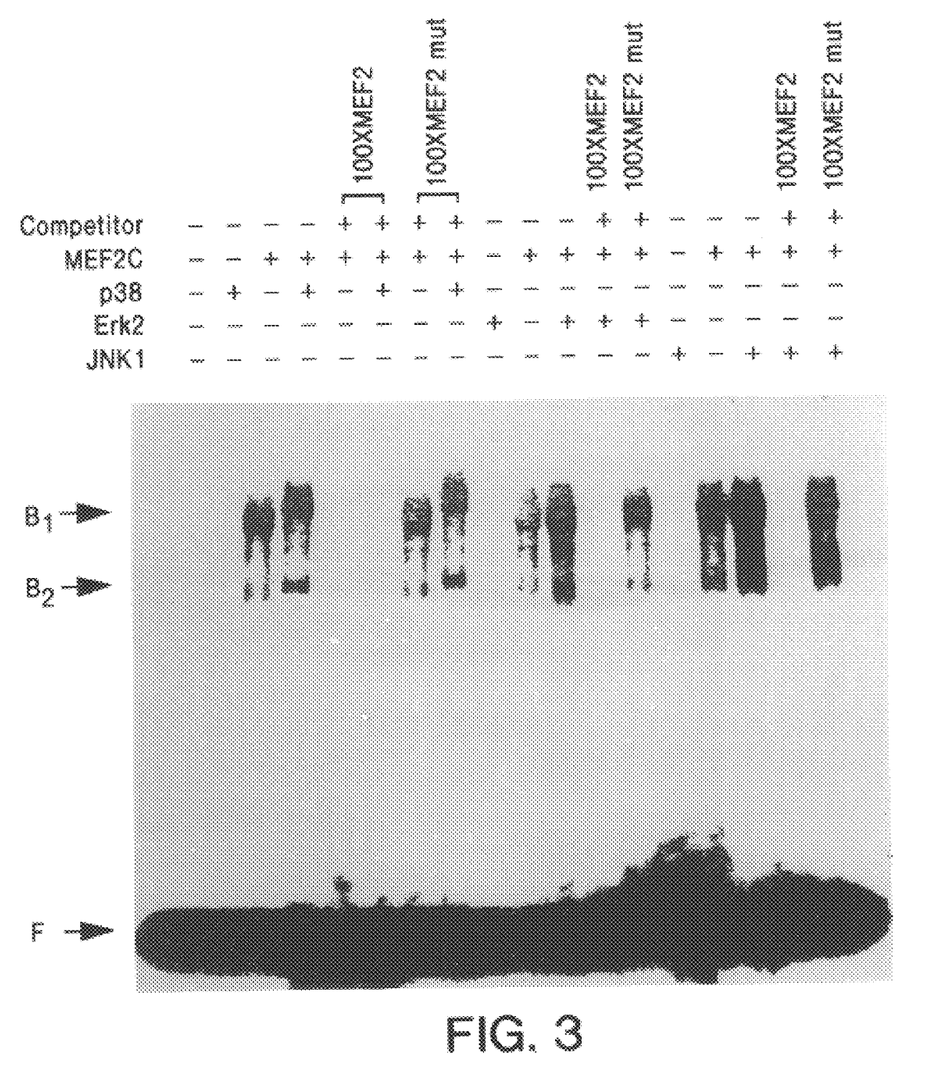
FIG. 3 shows an electrophoretic mobility-shift assay (EMSA) using oligonucleotide probes was double-stranded $^{32}$P-labeled oligonucleotide containing the MEF2 consensus binding site (Oligonucleotides sequence, MEF2C: GATCGCT<u>CTAAAAATAA</u>CCCTGTCG (SEQ ID NO: 1); MEF2Cmut: GATCGCT<u>CTAAACATAA</u>CCCTGTCG (SEQ ID NO: 2)) and the positions of free probe (F) and of bound probe ($B_1$ and $B_2$) are indicated by arrows.

Members of the MEF2 family bind to conserved A/T-rich DNA sequences—CTA[A/T]$_4$TAG/A—found in the regulatory regions of many muscle-specific genes (Y. -T. Yu et al., Genes and Develop. 6, 1783 (1992). Binding of MEF2C to the consensus site can be detected by electrophoretic mobility-shift analysis (EMSA) (J. F. Martin et al., Proc. Natl. Acad. Sci. USA, 90, 5282 (1993); J. C. McDermott et al., Mol. Cell. Biol. 13, 2564 (1994); D. Leifer et al., Proc. Natl. Acad. Sci. USA 90, 11546 (1993)). To test whether the phosphorylation of MEF2C alters MEF2C binding to its consensus DNA binding site the mobility of the MEF2C-DNA probe complex formed by MEF2C before and after its treatment with wtp38 was compared (FIG. 3). Phosphorylation of MEF2C by p38 did not reduce its interaction with the oligonucleotide but did caused a decreased mobility of this complex (FIG. 3B$_1$). Another band, indicated as B$_2$, formed in the presence of MEF2C; the mobility of this complex was also reduced after p38 treatment. In contrast treatment of MEF2C with either JNK1 or ERK2 failed to produced a similar change in the EMSA.

Binding of MEF2C to oligonucleotides containing the MEF2 consensus site determined by electrophoretic mobility-shift assay (EMSA). The oligonucleotide probe was double-stranded $^{32}$P-labeled oligonucleotide containing the MEF2 consensus binding site (Oligonucleotides sequence, MEF2C: GATCGCT CTAAAAATAACCCTGTCG (SEQ ID NO: 1); MEF2Cmut: GATCGCTCTAAACATAACCCTGTCG (SEQ ID NO: 2)) and the positions of free probe (F) and of bound probe (B$_1$ and B$_2$) are indicated by arrows. MEF2C was prepared by in vitro translation as described (Y. -T. Yu et al., Genes and Develop. 6, 1783 (1992)). p38 catalyzed phosphorylation of MEF2C was performed prior to incubation with DNA probes (B. Derijard et al., Cell 76, 1025 (1994).

EXAMPLE 5

Figure 4A:
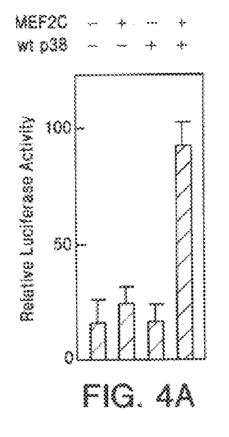
FIG. 4A shows phosphorylation of MEF2C by p38 increases the transactivation activity of MEF2C as shown by luciferase activity.
Figure 4B:
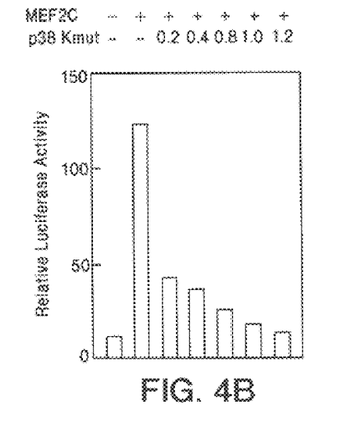
FIG. 4B shows activation of MEF2C by endogenous p38 as shown by luciferase activity.
Figure 4C:
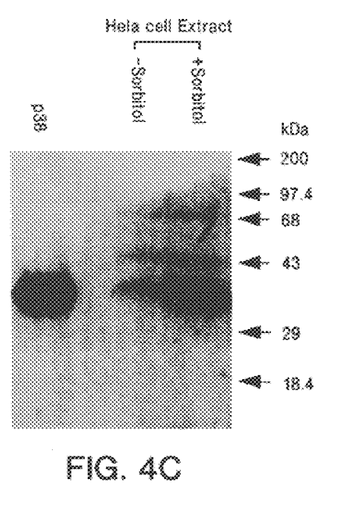
FIG. 4C is an in-gel kinase assay showing MEF2C kinase activity.

Hela cells were selected because we failed to detect MEF2C mRNA in this cell line using RNAse protection assays. In contrast this line has been shown to express transcripts for other members of the MEF2C family (R. E. Breitbart et al., Development 118, 1095 (1993); J. F. Martin et al., Cell. Biol. 14, 1647 (1994); Y. -T. Yu et al., Genes and Develop. 6, 1783 (1992)). A myosin light chain-2 (MLC2) promoter driven luciferase reporter (MLC2-luc) plasmid (S. A. Henderson et al., J. Biol. Chem. 264, 18142 (1989) was used because a MEF2 site is found in the MLC2 promoter and believed to play an important role in MLC gene expression. Expression of MEF2C in Hela cells minimally increased MLC2-luc reporter expression (FIG. 4A) Transfection of p38 alone does not have influence of the reporter expression but importantly when both p38 and MEF2C were co-transfected a significant increase in reporter gene expression was observed. When mutants of p38 without kinase activity (p38Kmut or TY mutant) were transfected together with MEF2C no enhancement of luciferase was observed (no data shown). These data support the contention that p38 can regulate the transactivation activity of MEF2C. Because overexpression of p38 alone does not influence the reporter gene expression this also suggests that p38 does not regulate the activity of other MEF2 family members which exist in Hela cells ((R. E. Breitbart et al., Development 118, 1095 (1993); J. F. Martin et al., Cell. Biol. 14, 1647 (1994); Y. -T. Yu et al., Genes and Develop. 6, 1783 (1992)). We have previously reported that increased extracellular osmolarity activates p38. To test if activated endogenous p38 would modulate the transactivation activity of the transient expressed MEF2C the following experiment was performed. Hela cells transfected with MEF2C and MLC2-luc reporter gene were treated with 0.4M sorbitol; this resulted in increased MLC2-luc gene expression (FIG. 4B). Importantly this stimulation is inhibited by co-transfection of a dominant-negative p38 mutant in which the ATP binding site was eliminated by mutating lys$^{53}$ to methionine (K mutant). The extent of inhibition produced by the K mutant of p38 depended on the amount of DNA used in the transfection (FIG. 4B). When we used another dominant negative p38 mutant, the TY mutant, a similar inhibition was observed. These data support the contention that endogenous p38 regulates the activity of MEF2C. Nonetheless this experiment does not exclude the possibility that dominant negative mutant of p38 binds to MEF2C thereby preventing other endogenous activators from interacting with MEF2C. To examine this question further an in-gel kinase assay was performed using MEF2C as the substrate within the SDS-gel. A protein with a mobility identical to of p38 was found to be responsible for MEF2C phosphorylation in lysates from sorbitol treated Hela cells (FIG. 4C). In studies not shown we determined that sorbitol treatment dramatically increased the enzymatic activity of p38 providing support for the interpretation of the in-gel kinase assay that the band detected reflects p38 activity. Collectively these data support the contention that in cells activation of p38 leads to phosphorylation of MEF2C and regulation of its transactivation activity.

The effect of over-expression wtp38 on the transactivation activity of MEF2C was examined by transfecting Hela cells with a rat MLC2 promoter driven luciferase reporter gene (MLC2-luc, 0.1 μg DNA) (S. A. Henderson et al., J. Biol. Chem. 265, 18142 (1989)) together with or without MEF2C (0.1 μg DNA) and/or p38 (0.2 μg DNA) in a mammalian expression vector pCDNA3 (The MEF2C cDNA containing the entire coding region without the last alternatively spliced exon and partial 5' and 3' untranslated region (49 to 2022 bp) was subcloned into pCDNA3 vector using BamHI and HindIII sites. The p38 cDNA is in HindIII and XbaI site of pCDNA3).

Activation of MEF2C by endogenous p38 was evaluated using 0.4 M sorbitol to stimulate the cells transfected with or without MEF2C and different amount (μg) of dominant negative p38 (p38Kmut) plasmid as indicated. Cells were harvested 8 h after 15 min sorbitol treatment. Results of one experiment are shown. Comparable results were obtained in two experiments. In all cotransfection experiments, the total amount DNA was kept constant using 1.5 μg per transfection by adding empty vector pCDNA3 DNA. Luciferase activity was assayed 48 h after transfection; the luciferase activity was normalized according to co-expressed β-gal activity from pCMBVβ (0.1 μg) (ClonTech).

MEF2C kinase activity was detected in an "in-gel kinase assay" using extracts of control or 0.4 M sorbitol treated Hela cell extracts. Recombinant His-MEF2C was immobilized in the SDS gel at a concentration of 0.2 mg/ml; 20 μg of protein from lysates, prepared as described (J. Han et al., J. Biol. Chem. 268, 25009 (1993)), of Hela cells treated with or without 0.4 M sorbitol for 15 min were electrophoresed.

2 μg of recombinant p38 was used as standard. The "in-gel kinase assay" was performed as described (H. -C. Wang et al., *Mol. Biol. Cell* 3, 1329 (1992)).

p38 is constitutive and ubiquitous with respect to tissue an cell type. In contrast MEF2C is tissue- or cell type-restricted (J. F. Martin et al., *Proc. Natl. Acad. Sci. USA* 90, 5282 (1993); J. C. McDermott et al., *Mol. Cell. Biol.* 13, 2564 (1994); D. Leifer et al., *Proc. Natl. Acad. Sci. USA* 90, 11546 (1993)). Clearly MEF2C plays an important role in myogenic events and regulates the expression of some muscle-specific genes (J. D. Molkentin et al., *Cell* 83, 1125 (1995). Our results suggest that studies of how the p38 pathway in muscle cells regulates the expression of MEF2C-dependent expression of muscle specific genes are warranted. In this regard we have recently described a p38 activator, an alternatively spliced isoform of MKK6, highly expressed in muscle but not other tissues (J. Han et al., *J. Biol. Chem.* 1996). In addition to muscle, MEF2C has been reported to be enriched in brain and spleen (J. F. Martin et al., *Proc. Natl. Acad. Sci. USA* 90, 5282 (1993); D. Leifer et al., *Proc. Natl. Acad. Sci. USA* 90, 11546 (1993); D. Leifer et al., *Neuroscience* 63, 1067 (1994)). A role for p38 has been proposed in neuronal apoptosis (Z. Xia et al., *Science* 270, 1326 (1995)) suggesting that further study of p38/MEF2C interactions in this setting might be fruitful. By using an RNA protection assay we have detected abundant MEF2C transcripts in primary monocytes and macrophages cell lines. DNA sequence analysis indicated that MEF2 site can be found not only in muscle-specific enhancer and promoter elements, but in promoters for the cytokines IFNα and IL-1β. Moreover multiple MEF2 or MEF2-like motifs also can be found in the 3'-end of many cytokine genes and may function in regulation transcription. Thus MEF2C may participate in regulation of cytokine gene expression in monocytes/macrophages. It is likely that studies of the role of p38 and MEF2C in these latter settings will prove to be useful in understanding the regulation of some genes involved in responses of the host innate immune system during infection and inflammation.

It is to be understood that while the invention has been described in conjunction with the detailed description thereof, that the foregoing description is intended to illustrate and not limit the scope of the invention, which is defined by the scope of the appended claims. Other aspects, advantages, and modifications are within the scope of the following claims.

What is claimed is:

1. A p38 MAP kinase reporter gene construct comprising:

a) a nucleotide sequence defining a reporter gene capable of expressing a detectable gene product upon expression;

b) a nucleotide sequence operably linked to said reporter gene defining a TATA box capable of binding a first transcription factor which interacts with and is activated by a phosphorylated second transcription factor, wherein said second transcription factor comprises a DNA binding domain and a MEF2C transcription activation domain; and c) a nucleotide sequence operatively linked to said TATA box that defines a DNA binding site for said DNA binding domain of said second transcription factor;

wherein upon phosphorylation of said second transcription factor by p38 MAP kinase, said second transcription factor binds to said DNA binding site and interacts with said first transcription factor bound to said TATA box, thereby activating expression of said reporter gene.

2. The reporter gene construct of claim 1 wherein said detectable gene product is selected from the group consisting of luciferase, beta-galactosidase and *Aequorea Victoria* jellyfish green fluorescent protein.

3. The reporter gene construct of claim 1 wherein said DNA binding protein is MEF2C and said DNA binding site is an MEF2C binding site.

4. The reporter gene construct of claim 1 wherein said DNA binding protein is a fusion protein having a DNA binding-site domain and a MEF2C transcription activation domain which is a substrate for p38 MAP kinase.

5. The reporter gene construct of claim 4 wherein said DNA binding site domain is derived from GAL4 and said DNA binding site is a GAL4 binding site.

6. A kit containing the reporter gene construct of claim 1.

7. A cell or cell line containing the reporter gene construct of claim 1.

8. A method for measuring the effect of a component on the p38 MAP kinase pathway in a reporter system comprising:
   a) contacting a sample containing said component with a p38 MAP kinase reporter gene construct according to claim 1 under conditions compatible with phosphorylation and gene expression in an expression admixture;
   b) maintaining said expression admixture under conditions sufficient for said phosphorylation and reporter gene expression; and
   c) measuring the amount of expressed reporter gene, and thereby measuring the effect of said component on said p38 MAP kinase pathway.

9. The method of claim 8 wherein said contacting in the expression admixture are conducted in vitro.

10. The method of claim 8 wherein said contacting in the expression admixture are conducted in a cell.

11. The method of claim 10 wherein said cell is selected from the group consisting of bacterial, yeast, and mammalian cells.

12. The method of claim 8 wherein said component is p38 MAP kinase.

13. The method of claim 8 wherein said component is a modulator of p38 MAP kinase.

14. The method of claim 8 wherein said component is a modulator of MEF2C.

* * * * *